US008416913B2

(12) United States Patent
Akino et al.

(10) Patent No.: US 8,416,913 B2
(45) Date of Patent: Apr. 9, 2013

(54) X-RAY CT SYSTEM, OBJECT-OUTLINE ESTIMATING METHOD, AND IMAGE RECONSTRUCTING METHOD

(75) Inventors: Naruomi Akino, Nasushiobara (JP); Satoru Nakanishi, Utsunomiya (JP); Tetsuya Horiuchi, Tsurugashima (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 358 days.

(21) Appl. No.: 12/045,966

(22) Filed: Mar. 11, 2008

(65) Prior Publication Data
US 2008/0226022 A1 Sep. 18, 2008

(30) Foreign Application Priority Data
Mar. 13, 2007 (JP) ................................. 2007-063450

(51) Int. Cl.
*A61B 6/03* (2006.01)
(52) U.S. Cl.
USPC .............................................. 378/4; 382/131
(58) Field of Classification Search ........ 378/4; 382/131
See application file for complete search history.

(56) References Cited

U.S. PATENT DOCUMENTS

| 4,223,384 | A |   | 9/1980  | Hounsfield et al. |         |
|-----------|---|---|---------|-------------------|---------|
| 4,550,371 | A | * | 10/1985 | Glover et al.     | 378/4   |
| 5,390,112 | A | * | 2/1995  | Tam               | 378/17  |
| 5,412,702 | A | * | 5/1995  | Sata              | 378/4   |
| 5,416,815 | A | * | 5/1995  | Hsieh             | 378/4   |
| 5,457,724 | A |   | 10/1995 | Toth              |         |
| 5,565,684 | A | * | 10/1996 | Gullberg et al.   | 250/363.04 |
| 5,640,436 | A |   | 6/1997  | Kawai et al.      |         |
| 5,739,539 | A | * | 4/1998  | Wang et al.       | 250/363.04 |
| 5,881,122 | A | * | 3/1999  | Crawford et al.   | 378/4   |
| 5,949,842 | A | * | 9/1999  | Schafer et al.    | 378/4   |
| 6,490,337 | B1| * | 12/2002 | Nagaoka et al.    | 378/20  |
| 7,995,703 | B2| * | 8/2011  | Yan               | 378/16  |
| 2004/0114727 | A1 |   | 6/2004 | Yan et al.        |         |
| 2005/0089138 | A1 |   | 4/2005 | Toth et al.       |         |

(Continued)

FOREIGN PATENT DOCUMENTS

| EP | 1 464 286 A1 | 10/2004 |
| JP | 2003-199739 | 7/2003 |
| WO | WO 2006/082557 A2 | 8/2006 |
| WO | WO 2006082557 A2 * | 8/2006 |

OTHER PUBLICATIONS

Sourbelle et al., Reconstruction from truncated projections in CT using adaptive detruncation, 2005, European Radiology, vol. 15, pp. 1008-1014.*

(Continued)

*Primary Examiner* — Toan Ton
*Assistant Examiner* — John Corbett
(74) *Attorney, Agent, or Firm* — Oblon, Spivak, McClelland, Maier & Neustadt, L.L.P.

(57) ABSTRACT

X-ray transmission data of a specific direction is extracted from X-ray transmission data obtained by rotating an X-ray tube irradiating an X-ray around an object. The outline of the object is calculated based on the X-ray transmission data of the specific direction. Then, based on this outline, the X-ray transmission data is corrected, and an image of the inside of the object is reconstructed from the corrected X-ray transmission data.

13 Claims, 17 Drawing Sheets

U.S. PATENT DOCUMENTS

2007/0076933 A1* 4/2007 Starman et al. ............... 382/128
2007/0092058 A1* 4/2007 Mattson ........................ 378/15
2007/0140416 A1* 6/2007 Nukui ............................ 378/19
2007/0268997 A1 11/2007 Zhu et al.

OTHER PUBLICATIONS

Herman, Correction for Beam Hardening in Computed Tomography, 1979, Physics in Medicine and Biology, vol. 24, No. 1, pp. 81-106.*

Kachelriess et al., Kymogram detection and kymogram-correlated image reconstruction from subsecond spiral computed tomography scans of the heart, 2002, Medical Physics, vol. 29, No. 7, pp. 1489-1503.*

Penssel et al., Hybrid Detruncation (HDT) Algorithm for the Reconstruction of CT Data, Presented Sunday, Nov. 28, 2004 at 11:45 AM, RSNA 2004, Code SSA17-07, 18 Pages.*

Gullberg et al., Boundary Determination Methods for Attenuation Correction in Single Photo Emission Computed Tomography, 1983, Emissions Computed Tomography, pp. 33-53.*

Kak et al., Principles of Computerized Tomographic Imaging, 1988, IEEE Press, ISBN 0-87942-198-3, Chapter 3.*

* cited by examiner

X-RAY CT SYSTEM, OBJECT-OUTLINE ESTIMATING METHOD, AND IMAGE RECONSTRUCTING METHOD

BACKGROUND OF THE INVENTION

1. Field of the Invention

The present invention relates to a technique of calculating the outline of an object from X-ray transmission data obtained by irradiating an X-ray to an object.

2. Description of the Related Art

A technique of irradiating an X-ray to an object, detecting the X-ray having transmitted through the object, reconstructing the obtained X-ray transmission data and thereby creating an image of the inside of the object has been provided. In this image reconstruction, it is possible to obtain a more accurate image if there is information on the outline of an object, such as the size of the object.

Conventionally, information on the outline of an object is calculated based on a scanogram. A scanogram can be obtained by capturing a scanogram of an object in advance. Then, based on the calculated outline of the object, such a scan plan is made that includes the conditions of a full scan of imaging while rotating an X-ray tube and a detector around the object. For example, the radiation dose of the X-ray is set smaller at a thinner portion of the object, whereby the amount of exposure in a full scan can be reduced, and a favorable image can be obtained.

In order to increase the image quality in reconstruction based on the X-ray transmission data obtained from the scan under the above conditions, it is preferred to change parameters used for reconstruction, depending on the size of the outline. A general method for ascertaining the size of a site in reconstruction is a method of extracting the outline of an object from an image having been restructured once. After the outline is extracted by this method, an image is reconstructed again by using parameters reflecting the outline. However, this requires the reconstruction twice. Therefore, a real-time characteristic is lowered. Moreover, it is necessary to reflect, on the second reconstruction, the result of measurement of the outline with an image obtained in the first reconstruction, which results in a complicated process.

Then, in order to solve this problem, as disclosed in Japanese Unexamined Patent Application Publication JP-A 2003-199739, the outline of an object is estimated from a scanogram, namely, 2-dimensional information obtained by scanning in the axial direction of the object as rotation of the X-ray tube around the object is stopped, the parameters are determined depending on the estimated outline size to perform a full scan, and an image is reconstructed based on the X-ray transmission data obtained in the full scan. According to this solution, image reconstruction needs to be performed only once.

However, in a case where a scanogram is used in estimation of the outline of an object, there is a possibility that the position of the object is different between when a scanogram is measured and when a full scan is performed, because the scanogram is obtained prior to the full scan. Therefore, the reconstructed image may be inaccurate when a full scan is performed by using parameters dependent on the outline obtained from the scanogram.

SUMMARY OF THE INVENTION

An object of the present invention is to provide an outline estimation technique by which it is possible to accurately calculate the outline of an object in a full scan and increase the real-time characteristic in image reconstruction. Moreover, another object of the present invention is to provide an image reconstructing technique by which it is possible to reconstruct a high-quality image based on the calculated outline.

In an outline estimating method according to a first embodiment of the present invention, from X-ray transmission data obtained by rotating an X-ray tube irradiating X-rays around an object, X-ray transmission data of several different directions is extracted, and the object outline are calculated based on the extracted X-ray transmission data. According to these embodiments, the outline of the object is calculated not from a reconstructed image, but from the X-ray transmission data obtained by rotating the X-ray tube irradiating X-rays around the object, namely, the sinogram obtained by full scan. Therefore, there is no need to execute the reconstruction process twice, and the real-time characteristic is increased. Moreover, since there is no time lag caused between capture of a scanogram and full scan, decrease of the accuracy of an image due to a deviation of the position of the object does not occur. Consequently, it is possible to obtain a reconstructed image with significantly higher accuracy than an image reconstructed by using an outline estimated from a scanogram.

Further, in an image reconstructing method according to a second embodiment of the present invention, from X-ray transmission data obtained by rotating an X-ray tube irradiating X-rays around an object, X-ray transmission data of several different directions is extracted, the outline of the object is calculated based on the extracted X-ray transmission data, the X-ray transmission data is corrected based on the calculated outline, and an image of the inside the object is reconstructed from the corrected X-ray transmission data. According to this embodiment, it is possible to reconstruct an image in consideration of a transmission characteristic of the X-ray resulting from the object outline. Therefore, it is possible to obtain a high-quality image that is as excellent as an image obtained in full scan according to a scanning plan based on the object outline obtained from a scanogram.

DETAILED DESCRIPTION OF THE EMBODIMENT

Figure 1:
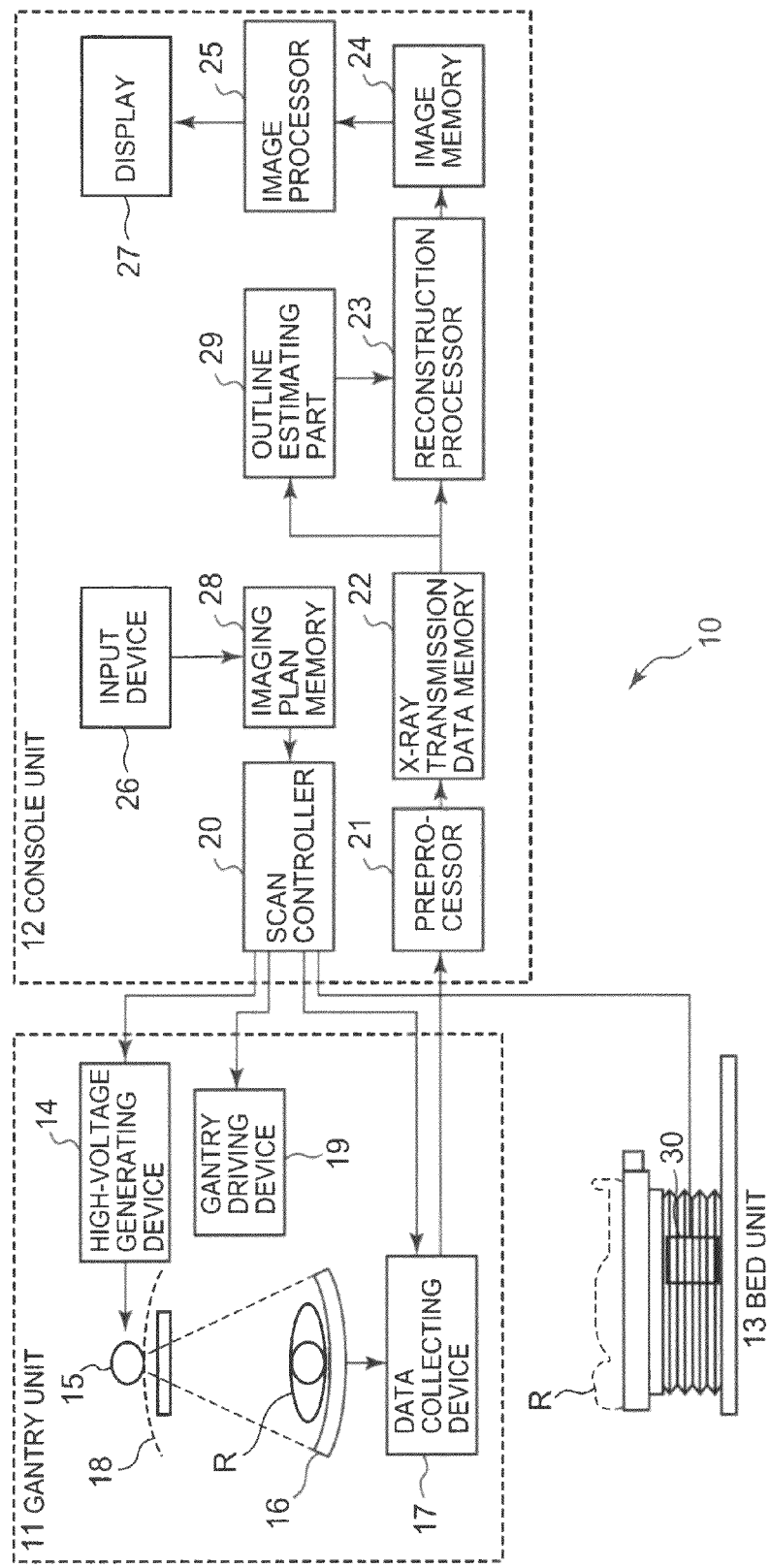
FIG. 1 shows a configuration of an X-ray CT system according to an embodiment of the present invention.

FIG. 1 is a configuration diagram of an X-ray CT system according to an embodiment of the present invention. An X-ray CT system 10 comprises a gantry unit 11, a console unit 12, and a bed unit 13.

The gantry unit 11 is a unit configured to irradiate an X-ray and detect the X-ray having transmitted through an object. The gantry unit 11 has an opening in which an object can be inserted. A rotating gantry 18 is housed inside the gantry unit 11. The rotating gantry 18 is provided with an X-ray tube 15 and an X-ray detector 16 facing each other across the opening. Moreover, a high-voltage generating device 14 paired with the X-ray tube 15, a gantry driving device 19 paired with the rotating gantry 18, and a data collecting device 17 paired with the detector 16 are placed inside the gantry unit 11.

The rotating gantry 18 is driven to rotate by a driving force of the gantry driving device 19. The rotating gantry 18 rotates around the opening. Moreover, the rotating gantry 18 rotates around an axis passing through a midpoint between the X-ray tube 15 and the X-ray detector 16.

The X-ray tube 15 receives supply of an electric current and application of a high voltage for heating a filament from the high-voltage generating device 14, thereby generating an X-ray. The generated X-ray is focused in a fan-shaped beam or a conical beam. As the high-voltage generating device 14, a high-frequency inverter type is employed: namely, a type of rectifying alternating-current power to a direct current, converting it to a high-frequency alternating current of a few kHz or more and boosting, and rectifying it again and applying.

The X-ray detector 16 includes X-ray detecting elements arranged in a plurality of lines and channels. The X-ray detector 16 detects the X-ray having transmitted through the object, and outputs the X-ray transmission data (raw data) as electric signals. The X-ray detecting element used generally is an indirect-conversion type that converts the X-ray into light with a phosphor such as a scintillator and further converts the light into electric charge with a photoelectric conversion element such as a photodiode, or a direct-conversion type that utilizes generation of electron-hole pairs within a semiconductor by the X-ray and movement thereof toward an electrode, namely, utilizes a photoconductive phenomenon.

The data collecting device 17 includes an I-V converter, an integrator, a preamplifier and an A/D converter for each of the X-ray detecting elements. The data collecting device 17 converts an electric current signal from each of the X-ray detecting elements into a voltage signal, periodically integrates and amplifies the voltage signal in synchronization with an X-ray irradiation cycle, and converts it into a digital signal. The data collecting device 17 outputs X-ray transmission data converted into the digital signal, to the console unit 12. To the outputted X-ray transmission data, tube position information is attached. The tube position information represents at what angle the X-ray tube 15 exists when the data is obtained.

In the bed unit 13, an object P is placed on a top board of a bed. Then, the bed unit 13 is driven to transport the object P in the direction of an opening axis by a bed driving device 30. Here, the object P may be transported in the opening axial direction by moving the rotating gantry 18 along the opening axis.

The console unit 12 controls to scan by the X-ray CT system 10 to obtain the X-ray transmission data. Then, the console unit 12 calculates the outline of the object P from the obtained X-ray transmission data, and corrects the X-ray transmission data based on the calculated outline. Then, the console unit 12 reconstructs an image based on the corrected X-ray transmission data. The X-ray transmission data used for calculating the outline is a sinogram obtained by full scan in which the X-ray tube 15 and the X-ray detector 16 are rotated around the object P. Hereinafter, the sinogram is simply referred to as the X-ray transmission data.

As a configuration to control the scan, the console unit 12 includes an input device 26, an imaging plan memory 28, and a scan controller 20. As a configuration to calculate the outline, the console unit 12 includes an outline estimating part 29. As a configuration to correct the X-ray transmission data based on the outline and reconstruct an image, the console unit 12 includes a preprocessor 21, an X-ray transmission data memory 22, a reconstruction processor 23, an image memory 24, and an image processor 25. Furthermore, the console unit includes a display device 27 configured to display the reconstructed image.

The imaging plan memory 28 stores the conditions of scanning each site. The imaging conditions include, for example, the rotation speed of the rotating gantry 18, the slice width, the fan angle, etc. at each site. The imaging conditions are inputted by an operator using an input device 26, or calculated based on inputted parameters, and stored in the imaging plan memory 28.

The scan controller 20 outputs control signals conforming to the imaging conditions stored in the imaging plan memory 28, to a high-voltage generating device 14, a gantry-driving device 19, a bed driving device 30, and a data collecting device 17, thereby controlling the full scan. In the full scan, an X-ray is irradiated to each position along the axial direction of the object P. In the full scan, the X-ray tube 15 and the X-ray detector 16 are rotated around the object P to irradiate an X-ray at each angle of the object P, and at the same time, the X-ray tube 15 and the X-ray detector 16 are moved in the axial direction of the object P relatively to the object P. For the full scan, the helical scan method or the conventional scan method may be employed depending on the control by the scan controller 20.

The preprocessor 21 applies sensitivity correction to the X-ray transmission data outputted from the data collecting device 17. In the sensitivity correction, the intensity of the X-ray is corrected. The preprocessor 21 then outputs the X-ray transmission data after the sensitivity correction, to the X-ray transmission data memory 22. The X-ray transmission data after the sensitivity correction is temporarily stored in the X-ray transmission data memory 22.

The outline estimating part 29 is a part configured to calculate the outline of an object from X-ray transmission data. The outline estimating part 29 extracts X-ray transmission data of a specific direction from the X-ray transmission data at the respective angles and tomographic positions obtained in the full scan, applies fan-parallel conversion to the X-ray transmission data of the specific direction, and thereafter calculates the outline of the object P from the converted X-ray transmission data. In the case of extracting X-ray transmission data of two directions orthogonal to each other, the outline estimating part 29 calculates the major diameter, the minor diameter, the shift amount in the major diameter direction, and the shift amount in the minor diameter direction. In the case of extracting X-ray transmission data of three or more directions, the outline estimating part 29 calculates the inclination of the object P in addition to the above. The tomographic position is a point along the body axis of the object P. The shift amount is the deviation amount of a position where the object P is placed, with respect to the center axis of the X-ray irradiation. The outline at the tomographic position where the X-ray transmission data of a specific direction does not exist is interpolated by using the X-ray transmission data of a specific direction at proximate tomographic positions.

The reconstruction processor 23 retrieves the X-ray transmission data stored in the X-ray transmission data memory 22, applies correction such as a scattered-radiation correction, BHC (beam hardening correction) and RASP process, based on the outline calculated by the outline estimating part 29. After the correction, the reconstruction processor 23 performs back projecting of the corrected X-ray transmission data, thereby reconstructing the image data. In a case where the X-ray transmission data is interpolated, the X-ray transmission data at a target slice position is obtained by 360-degree interpolation or 180-degree interpolation.

The reconstructed image data is temporarily stored in the image memory 24, and then sent to the image processor 25. Based on an operator's instruction inputted through an input device 26, the image processor 25 converts the image data into image data of a tomographic image of any cross section, a projection image from any direction, a 3-dimensional image by rendering or the like, and outputs it to the display device 27. The display device 27 displays the tomographic image or the like outputted from the image processor 25, on the monitor.

Figure 2:
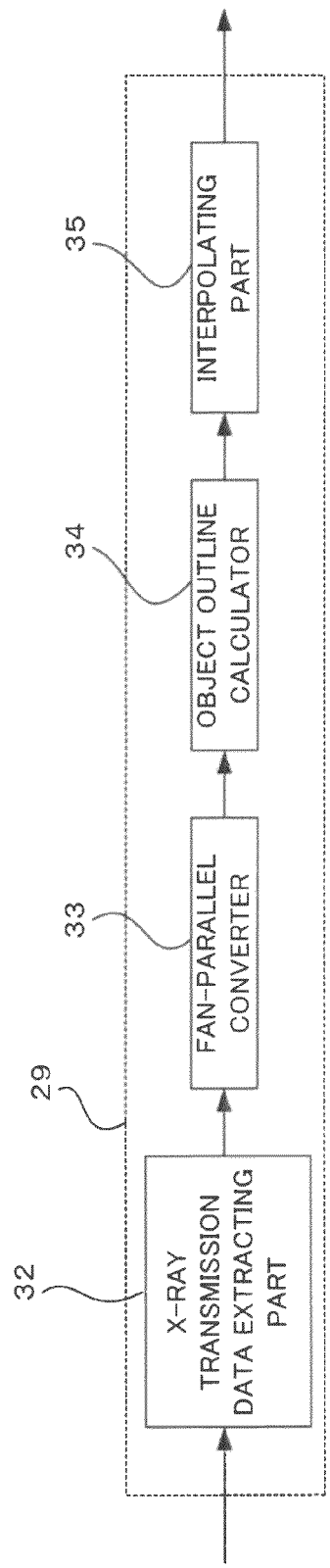
FIG. 2 shows a configuration of an outline estimating part of the X-ray CT system according to the embodiment of the present invention.

The calculation of the outline of the object P by the X-ray CT system 10 will be described in more detail. FIG. 2 is a block diagram of the outline estimating part 29. The outline estimating part 29 includes an X-ray transmission data extracting part 32, a fan-parallel converter 33, an object outline calculator 34, and an interpolating part 35.

The X-ray transmission data extracting part 32 extracts X-ray transmission data in a specific direction from the X-ray transmission data memory 22. The fan-parallel converter 33 converts the X-ray transmission data obtained with a fan beam, into X-ray transmission data of a parallel beam. The object outline calculator 34 calculates the major diameter, minor diameter and shift amount of the object from the X-ray transmission data converted by the fan-parallel converter 33. The interpolating part 35 interpolates the outline at a tomographic position not calculated by the object outline calculator 34, from the outline at each tomographic position calculated by the object outline calculator 34.

Figure 3:
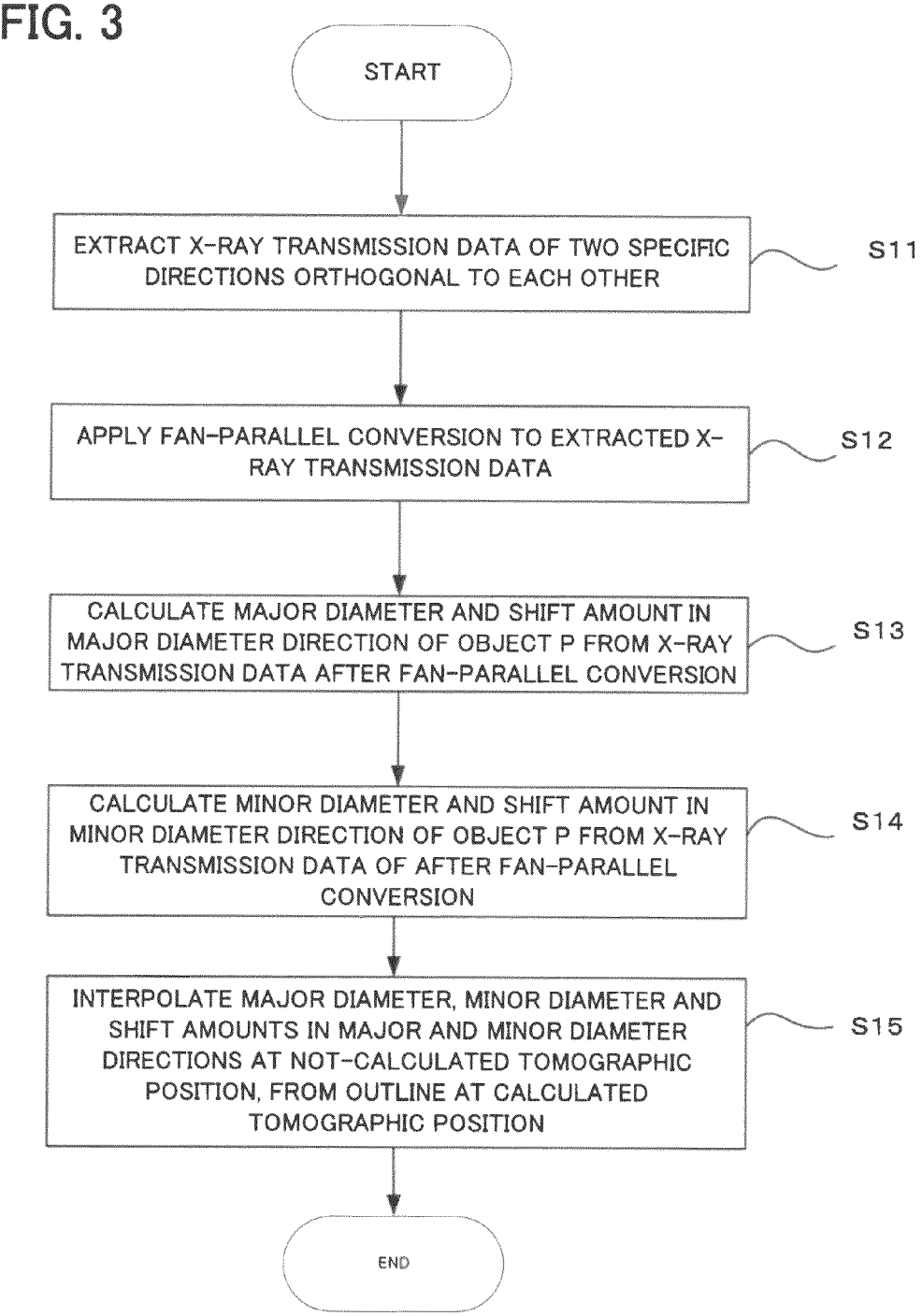
FIG. 3 is a flowchart showing an operation of outline calculation performed by the outline estimating part.

FIG. 3 is a flowchart showing an outline calculation operation performed by the outline estimating part 29. First, when X-ray transmission data is stored in the X-ray transmission data memory 22, the X-ray transmission data extracting part 32 extracts X-ray transmission data of two specific directions orthogonal to each other (S11). When the X-ray transmission data of the specific directions are extracted, the fan-parallel converter 33 applies fan-parallel conversion to the extracted X-ray transmission data (S12). When the fan-parallel conversion is applied, the object outline calculator 34 calculates the major diameter of the object P and the shift amount in the major diameter direction from the X-ray transmission data after the fan-parallel conversion obtained by irradiating the X-ray toward the front of the bed unit 13 (S13). Secondly, the object outline calculator 34 calculates the minor diameter of the object P and the shift amount in the minor diameter direction, from the X-ray transmission data after the fan-parallel conversion obtained by irradiating the X-ray from the side of the bed unit 13 (S14). Then, based on the calculated major diameter, minor diameter, shift amount in the major diameter direction and shift amount in the minor diameter direction, and also based on a distance between tomographic positions where the outline has been calculated and a tomographic position in the midway of the tomographic positions, the interpolating part 35 interpolates the major diameter, minor diameter, shift amount in the major diameter direction and shift amount in the minor diameter direction at the tomographic position in the midway (S15).

In the outline calculation operation, the X-ray transmission data extracting part 32 extracts X-ray transmission data on the top and side of the bed unit 13—that is, the two orthogonal directions—when the major diameter, minor diameter, shift amount in the major diameter direction and shift amount in the minor diameter direction of the object P are calculated. For example, assuming the front of the object P is 0°, only the X-ray transmission data when the X-ray tube 15 is placed at an angle of 0° or 180° or when the X-ray tube 15 is placed at an angle of 90° or 270° is extracted.

Figure 4:
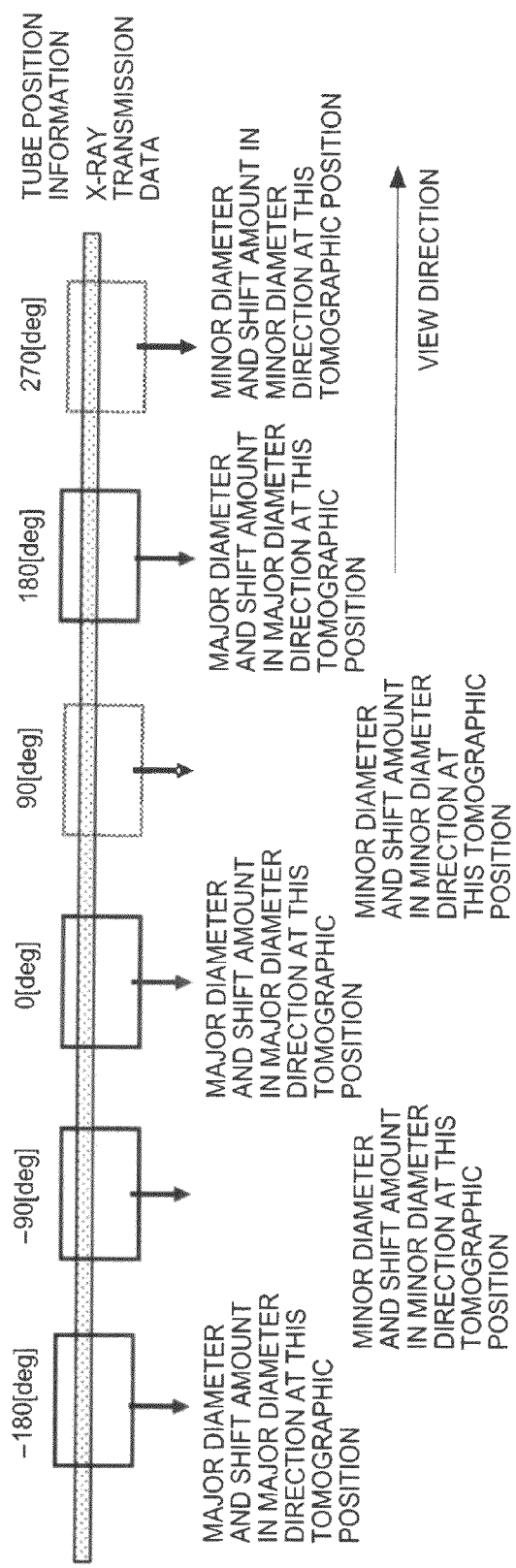
FIG. 4 schematically shows X-ray transmission data.

FIG. 4 shows a schematic view of the X-ray transmission data. The X-ray transmission data extracting part 32 refers to the tube position information, and extracts the X-ray transmission data when the X-ray tube 15 at each position in the axial direction of the object P is placed at an angle of 0° or 180° and the X-ray transmission data when the X-ray tube 15 at each position in the axial direction of the object P is placed at an angle of 90° or 270°.

Figure 5:
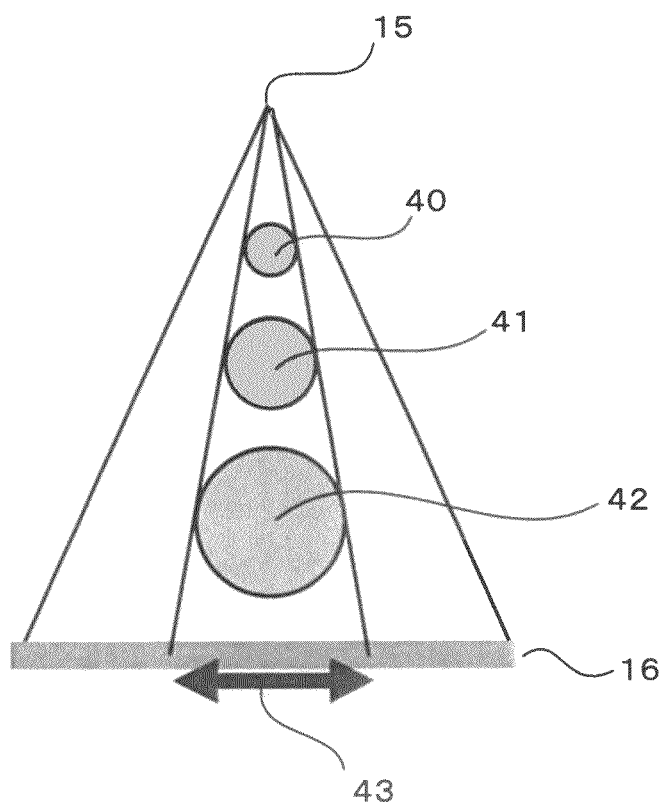
FIG. 5 schematically shows a relationship between the position of an object and the width of the object measured on the X-ray transmission data.
Figure 6:
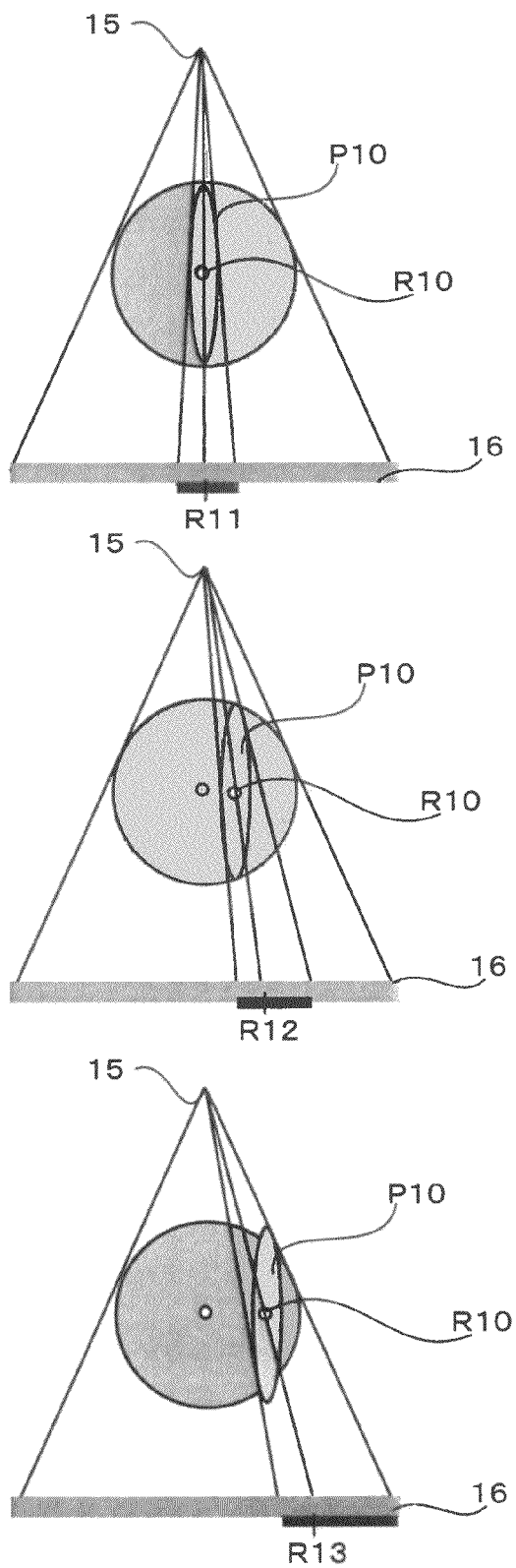
FIG. 6 schematically shows a relationship between the position of an object and the width and shift amount of the object measured on the X-ray transmission data.

Next, a general procedure of the fan-parallel conversion by the fan-parallel converter 33 will be explained. As shown in FIG. 5, from the X-ray tube 15, an X-ray is irradiated in the fan shape. In the case of measurement of the object using only this data, there arises a problem that, though circles 40, 41 and 42 have different sizes, the sizes become equal in the X-ray transmission data as shown by arrow 43. Moreover, in a case where the position of a center R10 of an object P10 varies as shown in FIG. 6, there arises a problem that the position thereof on the detector becomes R11, R12 and R13. Thus, by using adjacent data, the data is sorted as parallel beam data. In short, the abovementioned problems are solved by performing fan-parallel conversion.

In the fan-parallel conversion performed by the fan-parallel converter 33, one X-ray path to become parallel to a reference X-ray path is selected for each view angle. Alternatively, an approximately parallel path may be interpolated to become a parallel path.

One example of a formula of fan-parallel conversion to select data of the parallel path is shown below. A channel angle (ray angle) is determined as $\gamma$ (ch), a view angle as $\beta$ (pview), and an axis vertical to the parallel beam corresponding to each channel as an s axis. In addition, the maximum channel angle is determined as $\gamma m$. The parallel beam is expressed with $\beta$-s coordinates.

Figure 7:
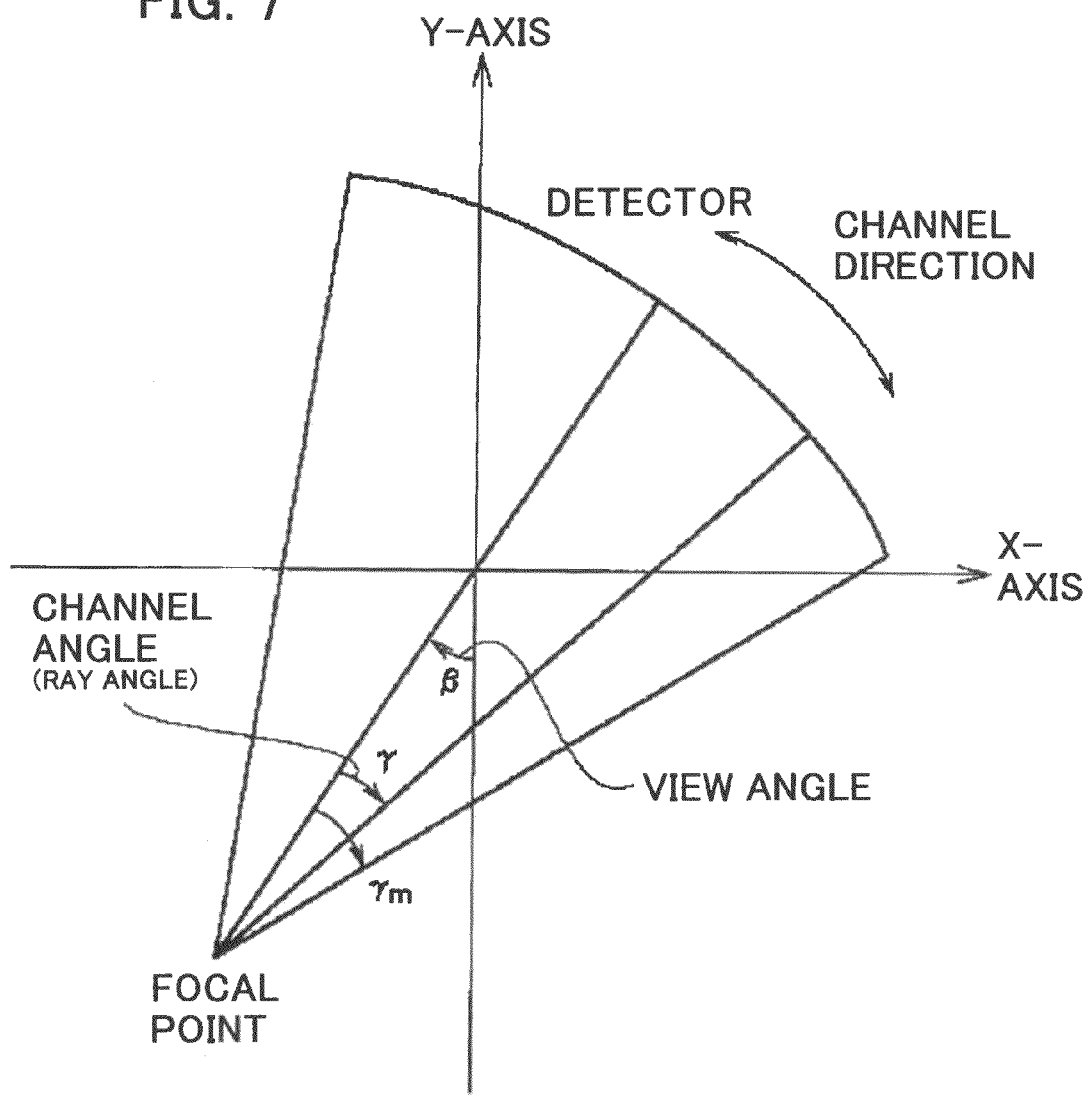
FIG. 7 is a view for describing a geometric plane on the x-y axes of a helical scan.
Figure 8:
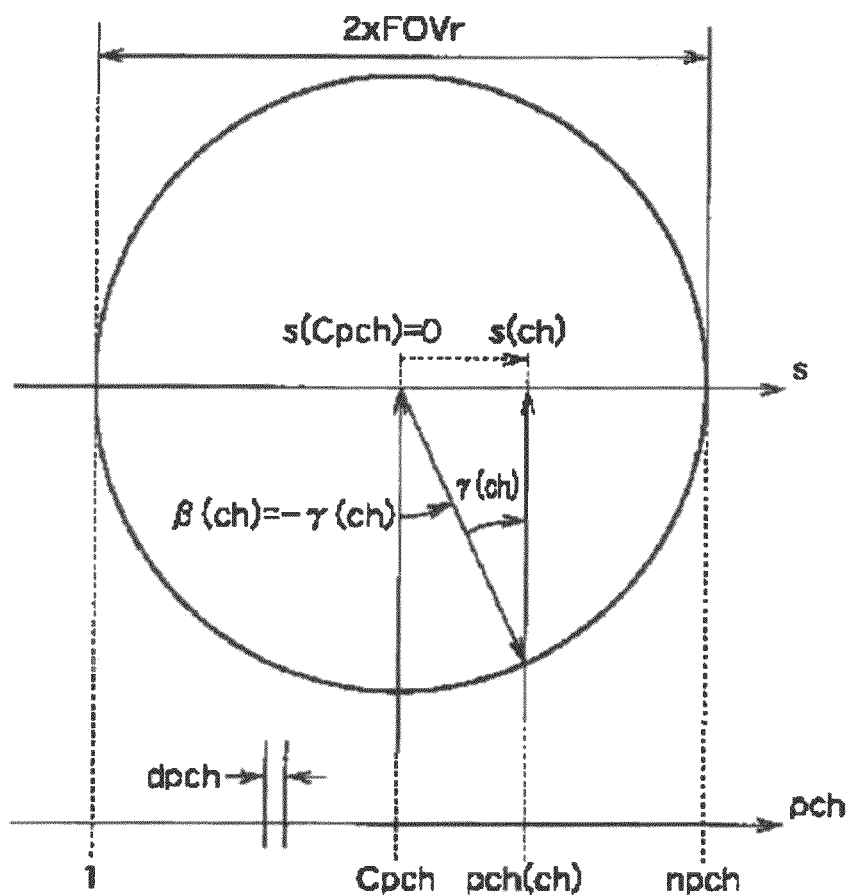
FIG. 8 is a view for describing a geometric space in conversion from divergent ray to parallel ray (fan-parallel conversion) in the embodiment of the present invention.

FIG. 7 shows a relationship between the channel angle (ray angle) $\gamma$ and the view angle $\beta$ in the geometry on the x-y plane. FIG. 8 shows geometry in the fan-parallel conversion. FIG. 9 is a view describing the concept of selection of the parallel beam for each view angle in the fan-parallel conversion.

Figures 9A, 9B:
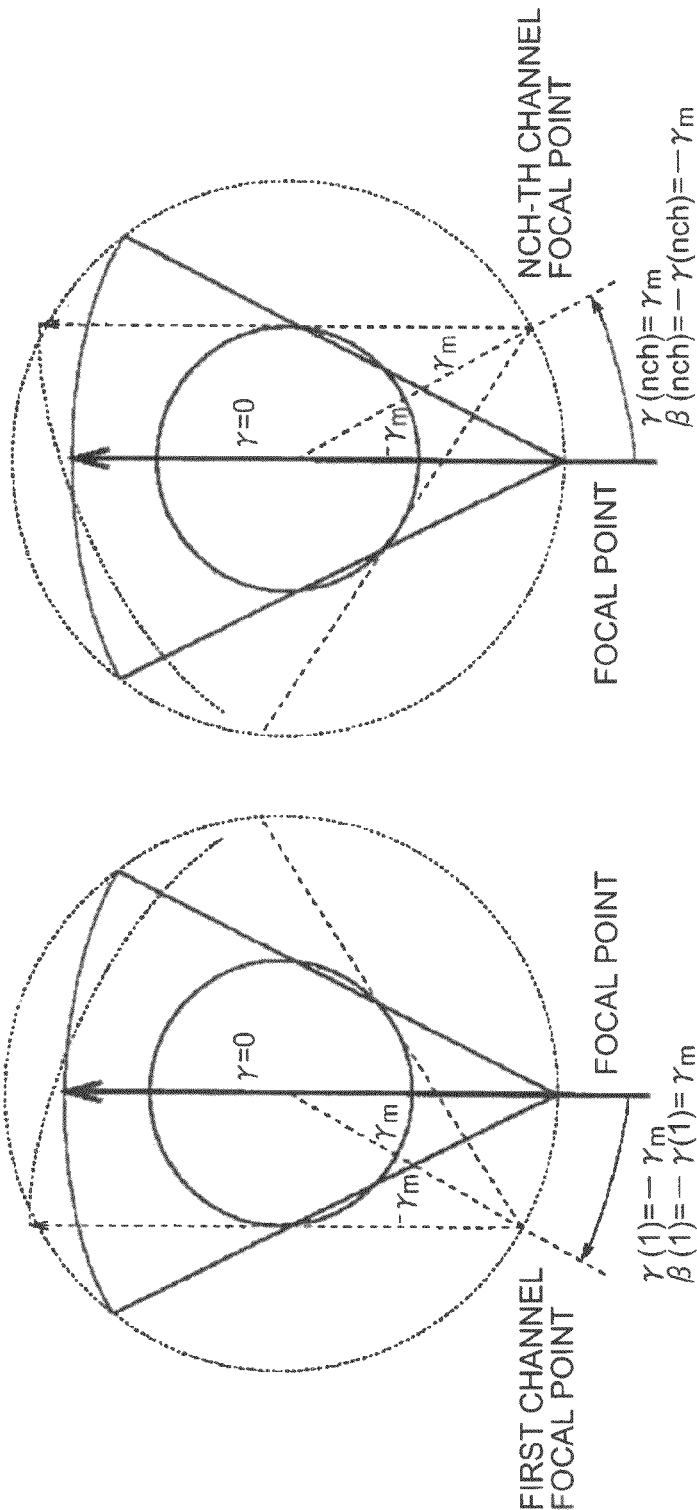
FIGS. 9A and 9B are views for describing a method of selecting a parallel beam of each view angle in the fan-parallel conversion.

As shown in FIG. 9A, when a path passing through the rotation center from a reference focal point is shown by solid-line arrow, in a case where the focal point becomes a focal point of an X-ray beam for a first channel, among fan beams, a beam (channel angle γ=−γm, view angle β=γm) shown by dashed-line arrow is selected as a path parallel to a reference path (γ=0). As shown in FIG. 9B, in a case where the focal point becomes a focal point of an X-ray beam for an nch channel, among the fan beams, a beam shown by dashed-line arrow is selected as a path (channel angle γ=γm, view angle β=−γm) parallel to the reference path (γ=0).

As shown in FIG. 8, assuming the coordinate on the s axis of the center channel (Cpch) in the parallel beam data is a reference value 0, coordinate S (ch) on the s axis of a certain channel can be obtained by the following Formula 1. The center channel in the fan beam data is determined as Cch, the center channel is the parallel beam data as Cpch, and the sampling pitch of the parallel beam as dpch. FanAngle refers to a fan angle, which is 2γm. FOVr refers to the maximum effective field of view radius.

The channel pch (ch) of the parallel beam data in a certain channel can be obtained by the following Formula 2. The sampling pitch dpch of the parallel beam data can be obtained by the following Formula 3.

$$S(ch) = FOVr \times \mathrm{Sin}(r(ch)) \qquad \text{[Formula 1]}$$
$$= FOVr \times \mathrm{Sin}\left[\frac{FanAngle}{nch} \cdot (ch - Cch)\right]$$

$$Pch(ch) = \frac{S(ch)}{dpch} + Cpch \qquad \text{[Formula 2]}$$

Wherein,
Cch: the center channel in the fan beam data
Cpch: the center channel in the parallel beam data $$dpch(ch) = 2 \times FOVr/(npch-1): \qquad \text{[Formula 3]}$$

the sampling pitch of the parallel data

Variables relating to the fan beam are defined as follows. nch denotes the number of channels for the detector. Cch denotes the center channel number. The center channel number Cch varies depending on the QQ offset amount. QQ shows the QQ (Quarter-Quarter) offset element and is determined depending on the system that implements to the present embodiment. The QQ offset is a method for improving the spatial resolution by attaching the detector with ¼ channel off in the channel direction to the center line. When the detector is offset correctly, normally, QQ=0.25. In addition, as long as the QQ offset is correctly done—e.g., when the number of channel is 896—the center channel number Cch comes to 448.25.

nview denotes the number of X-ray transmission data per rotation, such as 900 and 1200. raw(view, ch) denotes raw data in fan bean of X-ray transmission data of view-th of a ch-th channel.

On the other hand, the variables of the parallel beam are defined as follows. npch refers to the number of channel of the parallel beam data. Cpch refers to the center channel number of the parallel beam data. For example, when the channel number is 896, the center channel number comes to 448.5. npview refers to the number of the X-ray transmission data per rotation in the parallel beam. praw (pview, pch) shows a raw data in the parallel beam of the pview X-ray transmission data of the pch channel.

Furthermore, pconv (pview,pch) refers to a convolution data treated by the filter correction processing by means of the pview convolution method of the pch channel. dc refers to a pitch of the resampling/centering point, and ncp refers to the number of the resampling/centering point. pcent (pview, cp) shows the data treated by the resampling/centering processing.

Further, γ denotes a channel angle of the detector channel to be attended, γm denotes a half of the fan angle, β0 denotes a view angle of the X-ray transmission data to be attended and β denotes a relative view angle of each channel.

In addition, regarding each function, floor( ) refers to a cutoff integral function, Pv(pch) refers to a relative X-ray transmission data number of the pch channel, and Pch(pch) refers to a channel number of the pch channel.

The channel number of the parallel beam data is now obtained. Firstly, the abovementioned formula 1 is substituted into the formula 2 to obtain the following formula 4. By transforming it, the following formula 5 is obtained.

$$Pch(ch) = \frac{FOVr}{dpch} \times \mathrm{Sin}\left[\frac{FanAngle}{nch} \cdot (ch - Cch)\right] + Cpch \qquad \text{[Formula 4]}$$

$$\therefore ch(pch) = \qquad \text{[Formula 5]}$$
$$\frac{nch}{FanAngle} \times \mathrm{Sin}^{-1}\left[\frac{2 \cdot (PCH - Cpch)}{npch - 1}\right] + Cch \equiv PCh(pch)$$

As shown in FIG. 8, the following formula 6 is established.

$$\beta(ch) = -\gamma(ch) = \frac{FanAngle}{nch} \cdot (Cch - ch) \qquad \text{[Formula 6]}$$

$$\therefore Pv(pch) = \beta(ch(pch)) \cdot \frac{nview}{360} \qquad \text{[Formula 7]}$$
$$= \frac{FanAngle}{nch} \cdot \frac{nview}{360} \cdot (Cch - Pch(pch))$$

Accordingly, the relative X-ray transmission data number Pv at the pch channel is obtained by the following formula 7. As such, the parallel beam praw (pview, ch) is selected with respect to the required channel.

Figure 10:
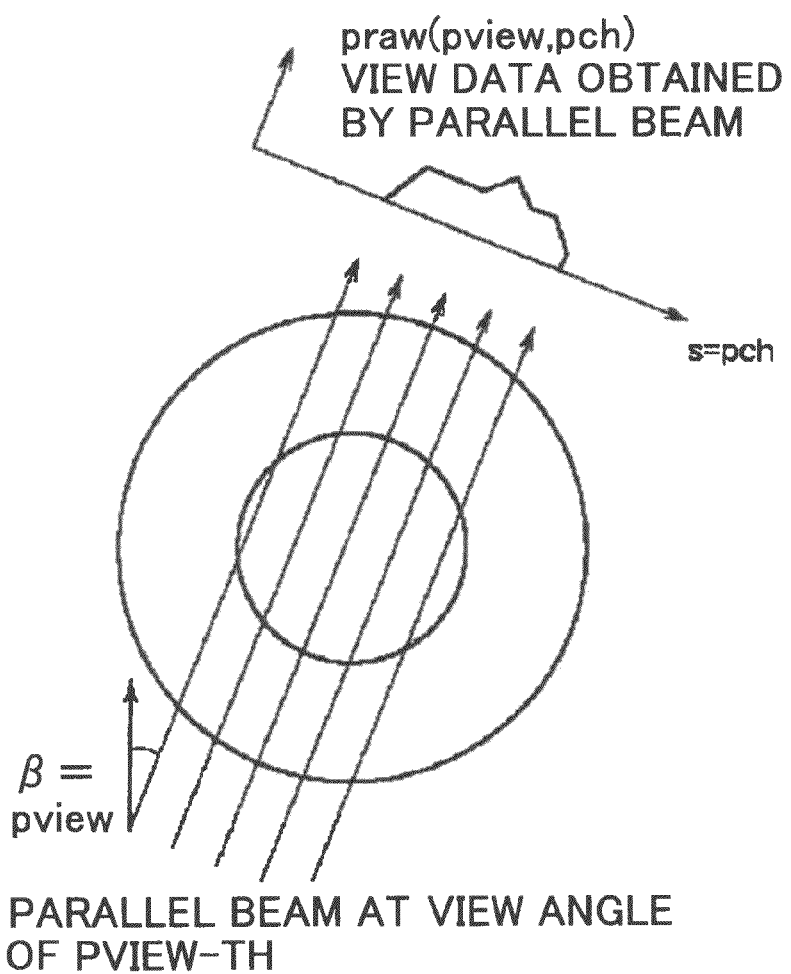
FIG. 10 is a view for describing a relationship between a generated parallel beam and a view axis.

The parallel beam praw (pview, ch) to the required channel can be generated by the following formula. FIG. 10 shows the relationship between (each channel of) the parallel beam selected for each view angle and the s axis where the parallel beam is projected. The s axis is vertical to the view angle to be projected. The value of the positional correction in the channel direction is calculated taking this s axis as a basis.

$$IPch = \mathrm{floor}[Pch(pch)] \qquad \text{[Formula 8]}$$

$$IPv = \mathrm{floor}[Pv(pch)] \qquad \text{[Formula 9]}$$

In the abovementioned formula 8 and formula 9, floor( ) refers to a cutoff integral function.

Herein, the following formula 10 and 11 are used to obtain the formula 12.

$$\beta 0(pview) = \frac{180 \cdot (pview - 1)}{npview} \qquad \text{[Formula 10]}$$

$$\beta 0 = (view) = \frac{180 \cdot (view - 1)}{nview} \qquad \text{[Formula 11]}$$

$$v = \mathrm{view}(pview) = \frac{2 \cdot npview}{nview} \cdot (pview - 1) + 1 \qquad \text{[Formula 12]}$$

In addition, the weighted function is defined as the following formula 13 and 14.

$$Wv = Pv[pch] - IPv \quad \text{[Formula 13]}$$

$$Wch = Pch[poh] - IPch \quad \text{[Formula 14]}$$

That is, the parallel beam praw to a necessary channel can be obtained by the following formula 15 (pview, ch).

$$praw(pview, poh) = raw(v+Pv(pch), pch) = [raw(v+IPv, IPch) + Wch \times (raw(v+IPv, IPch+1) - raw(v+IPv, IPch))] \times [1-Wv] + [raw(v+IPv+1, IPch) + Wch \times (raw(v+IPv+1, IPch+1) - raw(v+IPv+1, IPch))] \times Wv \quad \text{[Formula 15]}$$

Figure 11:
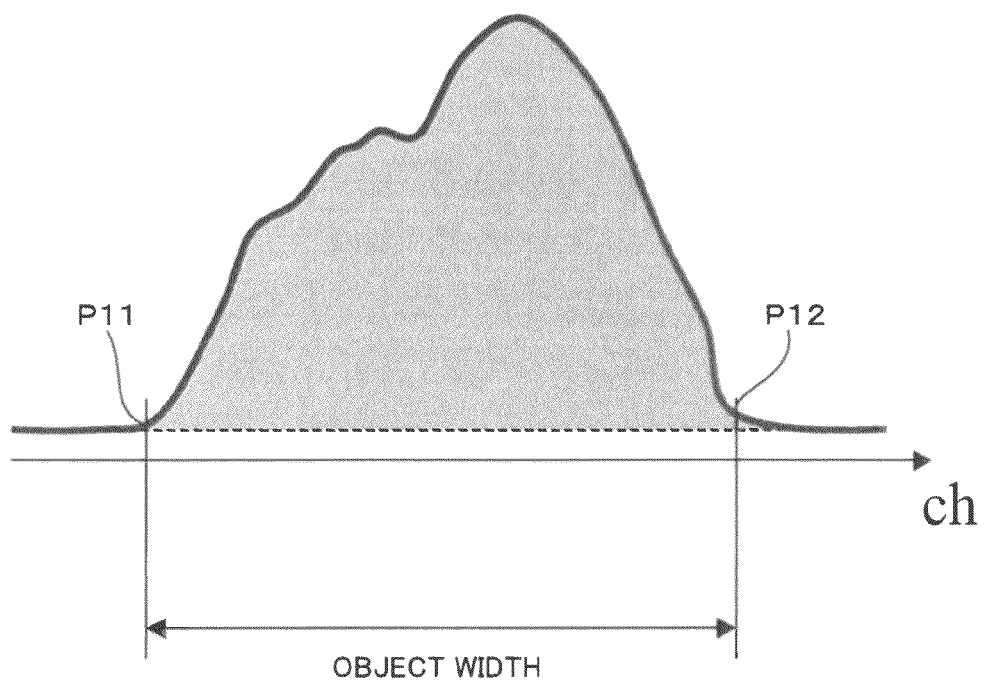
FIG. 11 is an example of a profile of the X-ray transmission data after the fan-parallel conversion.

Next, FIG. 11 shows an example of calculation of the major diameter, minor diameter and shift amount of the object P by the object outline calculator 34. FIG. 11 is an example of the profile of the X-ray transmission data and the fan-parallel conversion. The horizontal axis takes the position, and a distance between point P11 and point P12 is a width W of the object P.

The object outline calculator 34 calculates the distance between the point P11 and the point P12 as the major diameter of the object P from the X-ray transmission data at 0° and 180°, and calculates the distance between the point P11 and the point P12 as the minor diameter of the object P from the X-ray transmission data at 90° and 270°. Furthermore, from the difference between the middle point between the point P11 and the point P12 and the center of the X-ray transmission data profile, the shift amount in the major diameter direction and the minor diameter direction is obtained.

Figure 12:
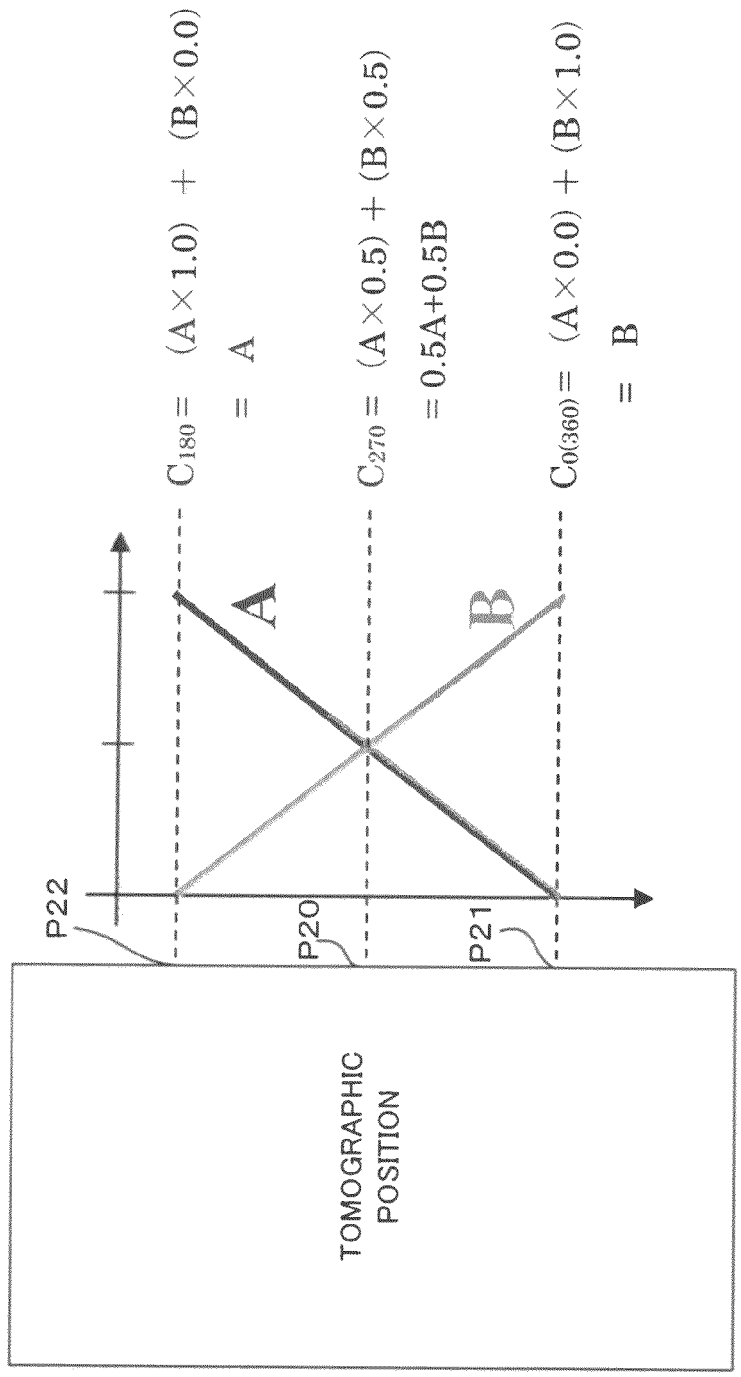
FIG. 12 schematically shows a process of interpolating a tomographic position other than a tomographic position to which X-rays are irradiated from a specific direction.

Next, FIG. 12 schematically shows a process executed by the interpolating part 35 to interpolate a tomographic position other than a tomographic position to which X-rays have been irradiated from a specific direction.

The interpolating part 35 weights and normalizes the major diameter, minor diameter, shift amount in the major diameter direction and shift amount in the minor diameter direction at each tomographic position calculated by the object outline calculator 34 in response to the distance between the tomographic position where the outline is calculated and the tomographic position to store the outline. For example, in the case of denoting a major diameter of a tomographic position P22 where X-rays are irradiated from an angle of 180° by A and denoting a major diameter of a tomographic position P21 where X-rays are irradiated from an angle of 0° by B, thereby obtaining a major diameter C of an object P at a tomographic position P20 where X-rays are irradiated from an angle of 270° that is a middle point, it is possible to obtain the major diameter C at the tomographic position where X-rays are irradiated from the angle of 270°, by calculating C=0.5A×0.5B, because the ratio between a distance from P20 to P21 and a distance from P20 to P22 is 0.5:0.5. Moreover, it is possible to obtain the major diameter C at the tomographic position where X-rays are irradiated from an angle of 315°, by calculating C=0.25A×0.75B, because the ratio between a distance from P20 to P21 and a distance from P20 to P22 is 0.25:0.75. Accordingly, the outline at the tomographic position is interpolated by weighting the calculated outline with the reverse ratio of the distance.

Figure 13:
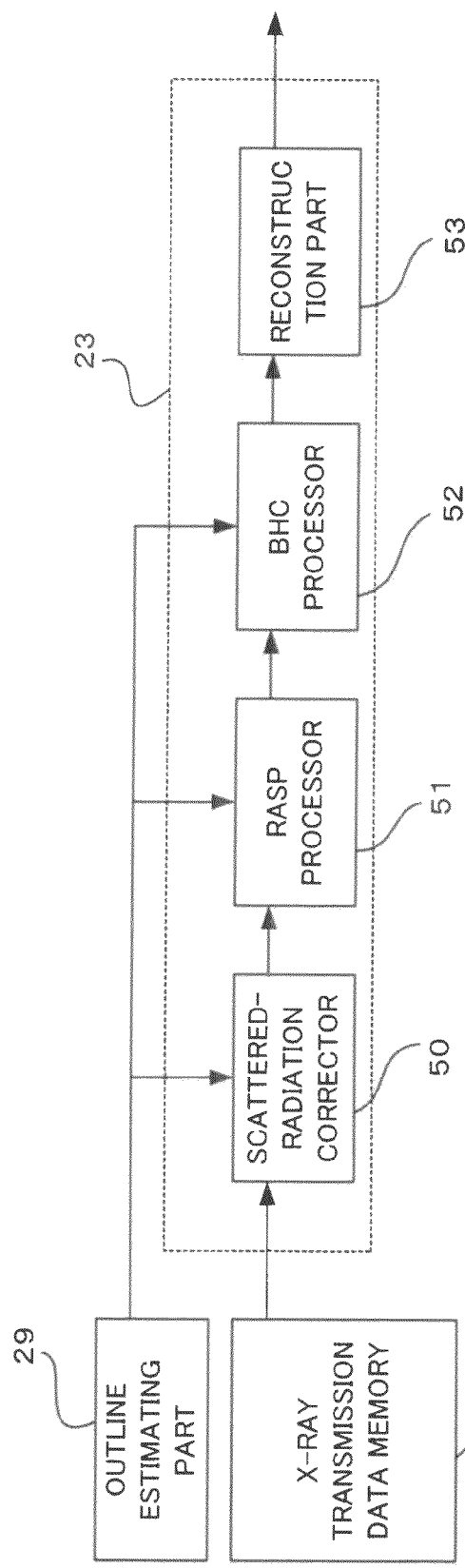
FIG. 13 shows a configuration of a reconstruction processor.

In this manner, the outline estimating part 29 calculates the object outline. Next, correction of X-ray transmission data before image reconstruction by the reconstruction processor 23 will be described in more detail. FIG. 13 is a block diagram of the reconstruction processor 23.

The reconstruction processor 23 performs various corrections by using the object outline calculated by the outline estimating part 29, and executes the reconstruction process.

The reconstruction processor 23 includes a scattered-radiation corrector 50, a RASP processor 51, a BHC processor 52, and a reconstruction processor 53.

The scattered-radiation corrector 50 performs correction to eliminate scattered-radiation components from the X-ray transmission data by using the outline obtained by the outline estimating part 29. The X-ray CT system 10 is basically configured to measure the degree of attenuation on a path between elements of the X-ray tube 15 and the X-ray detector 16. Since scattered radiation is certainly undesirable, a collimator removing scattered-radiation is interposed between the X-ray tube 15 and the X-ray detector 16 so as to prevent scattered radiation from entering into the X-ray detector 16. That is, only attenuation on a straight line is measured. As the X-ray CT system 10, a multi-tube type of X-ray CT system has been realized, which comprises a plurality of pairs of the X-ray tube 15 and the X-ray detector 16 and obtains a plurality of sets of the X-ray transmission data simultaneously. A problem here is that scattered radiation may enter into the X-ray detector 16. It is difficult to remove such scattered radiation. A solution for this problem is to, by using the object outline, estimate the amount of X-ray scattered at the edge of the outline and correct the intensity of the X-ray actually entering the X-ray detector 16 with the scattered radiation. In this case, it is possible to more accurately correct, by using the outline calculated by the outline estimating part 29.

Figure 14:
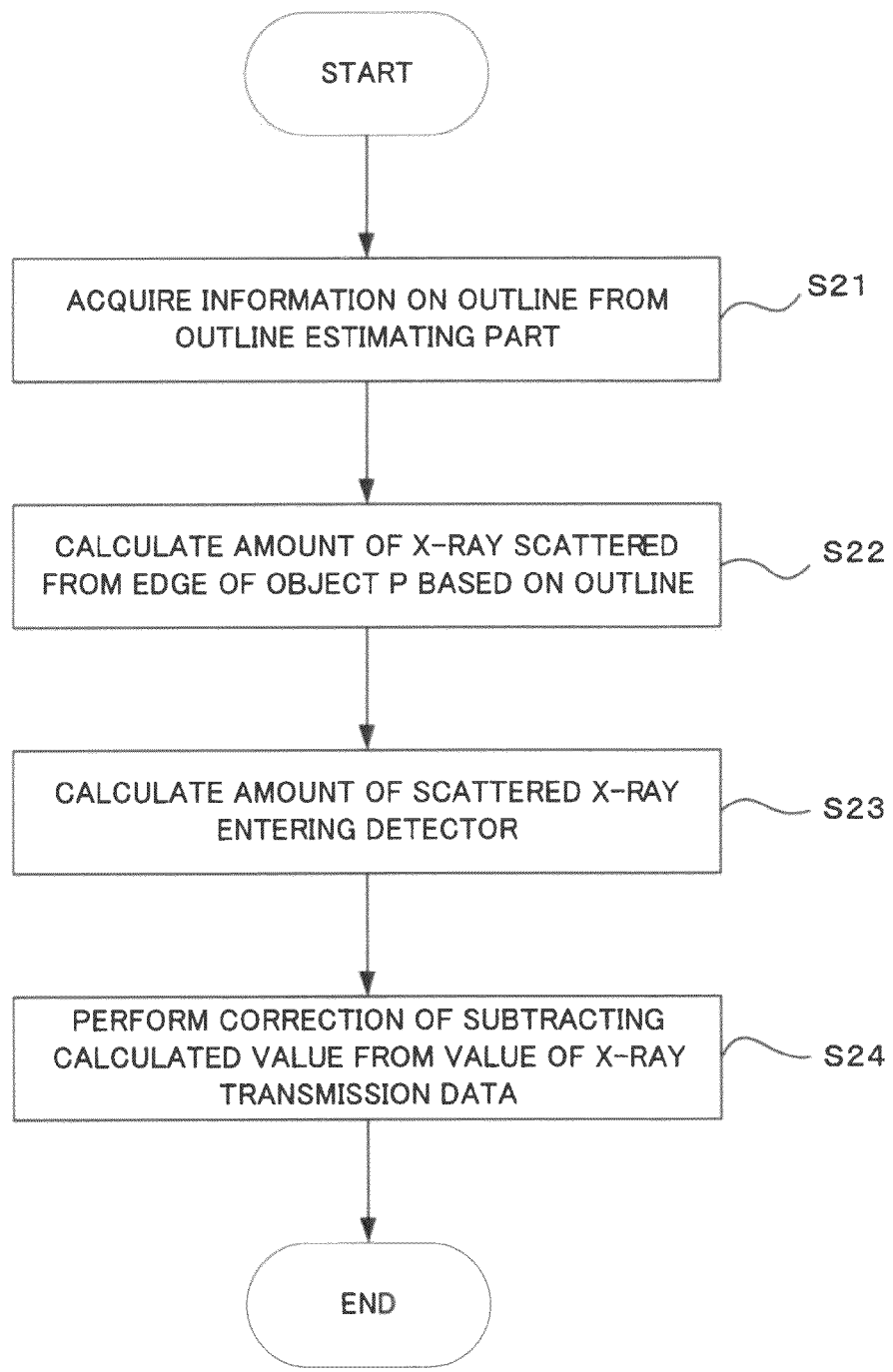
FIG. 14 is a flowchart showing an operation of scattered radiation correction performed by a scattered radiation corrector.

FIG. 14 is a flowchart showing an operation of correcting scattered radiation by the scattered radiation corrector 50. Firstly, the scattered radiation corrector 50 acquires the outline information from the outline estimating part 29 (S21). When acquiring the outline information, the scattered radiation corrector 50 calculates the amount of X-ray scattered from the edge of the object P based on the outline (S22). Then, it calculates the amount of scattered X-ray entering the X-ray detector 16 (S23). When calculating the entering amount, the scattered radiation corrector 50 performs correction by subtracting the calculated value from the value of the X-ray transmission-data (S24).

The RASP processor 51 selectively passes the X-ray transmission data through a low-pass filter for noise removal to become the basis of the RASP artifact, by using the outline obtained by the outline estimating part 29. Part of the X-ray transmission data is passed through the low-pass filter, whereas part of the X-ray transmission data is not passed through the low-pass filter. It is determined depending on the thickness of the outline whether to pass through the low-pass filter.

The RASP artifact is a raspatory-shaped artifact generated by noise received by the X-ray detector 16. When the X-ray transmission data with low S/N ratio is passed through the low-pass filter, data obtained by passing through the object P is easily lost. Attenuation of the intensity of the X-ray passed through a thick part of the outline of the object P is large, which worsens the S/N ratio. The RASP processor 51 passes, through the low-pass filter, the X-ray transmission data obtained by passing through a thin part of the outline where data obtained by passing through the object P is not easily lost even when passed through the low-pass filter. On the other hand, the RASP processor 51 does not pass, through the low-pass filter, the X-ray transmission data obtained by passing through a thin part of the outline where data obtained by passing through the object P is easily lost when passed through the low-pass filter.

Figure 15:
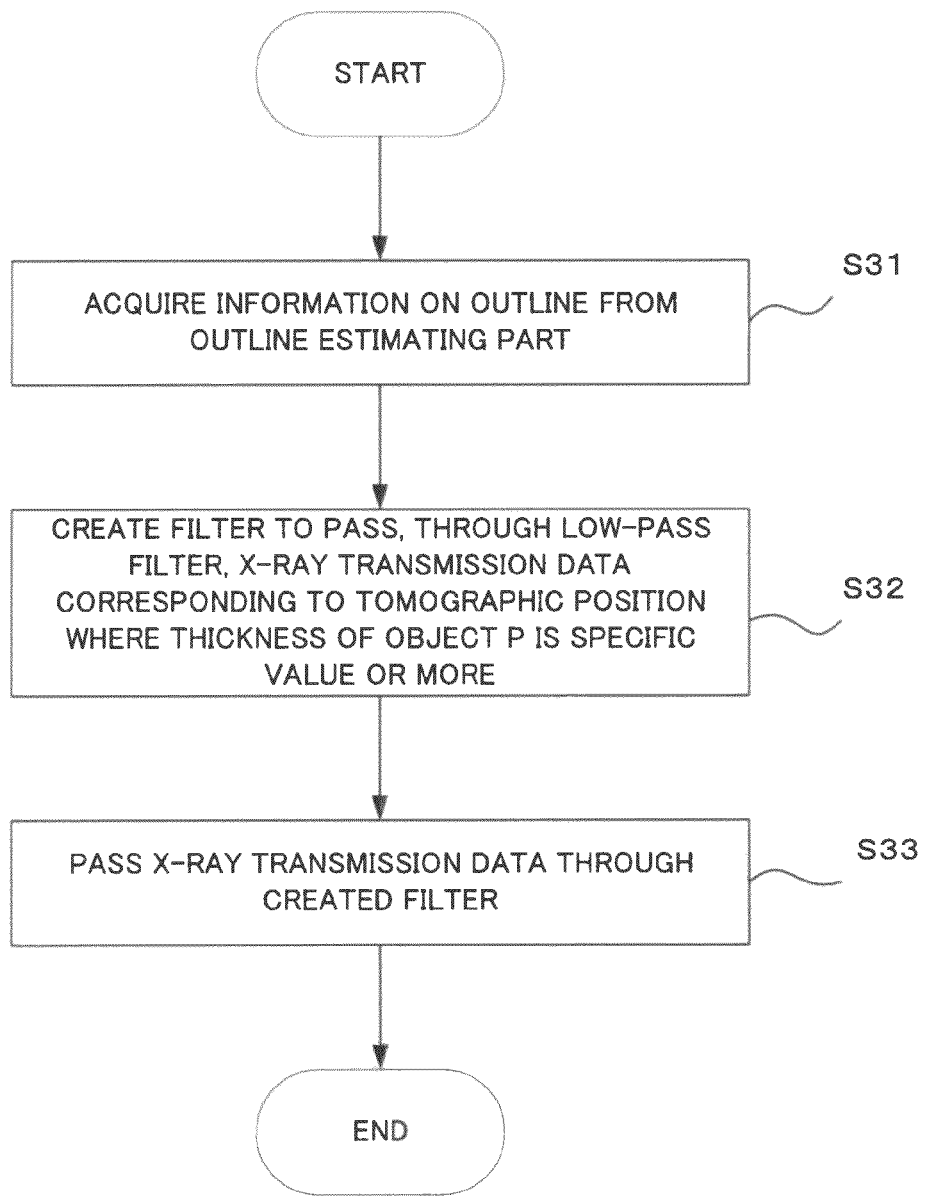
FIG. 15 is a flowchart showing an operation of a RASP process performed by a RASP processor.

FIG. 15 is a flowchart showing an RASP processing operation by the RASP processor 51. Firstly, the RASP processor 51 retrieves information on the outline of the object P from the outline estimating part 29 (S31), and creates a filter to pass, through the low-pass filter, the X-ray transmission data corresponding to a tomographic position where the thickness of object P is a specific value or more (S32). The RASP processor 51 previously stores the specific value, and retrieves the specific value to compare with the thickness calculated from the outline. In a case where the thickness is the certain value or more as a result of the comparison, the RASP processor 51 creates a low-pass filter for the X-ray transmission data obtained by passing through the outline position having the thickness.

When creating the filter, the RASP processor 51 passes the X-ray transmission data through the filter (S33). Consequently, the RASP artifact is removed while the data obtained by passing the X-ray is not lost by the low-pass filter.

The BHC processor 52 executes the BHC process of using the outline obtained by the outline estimating part 29 and adjusting values of the X-ray transmission data in consideration of the influence of the beam hardening effect.

Since the X-ray is not monochromatic X-ray but multicolor X-ray, the X-ray spectrum varies depending on a site to pass through. Therefore, the X-ray becomes hard to attenuate gradually. This is called beam hardening (BH). Although the X-ray detector 16 must be able to obtain determined count depending on the transmission length of the object P, the count may be more than the appearance actually because the X-ray becomes hard to attenuate. A method for correcting it is called beam-hardening correction (BHC).

Figure 16:
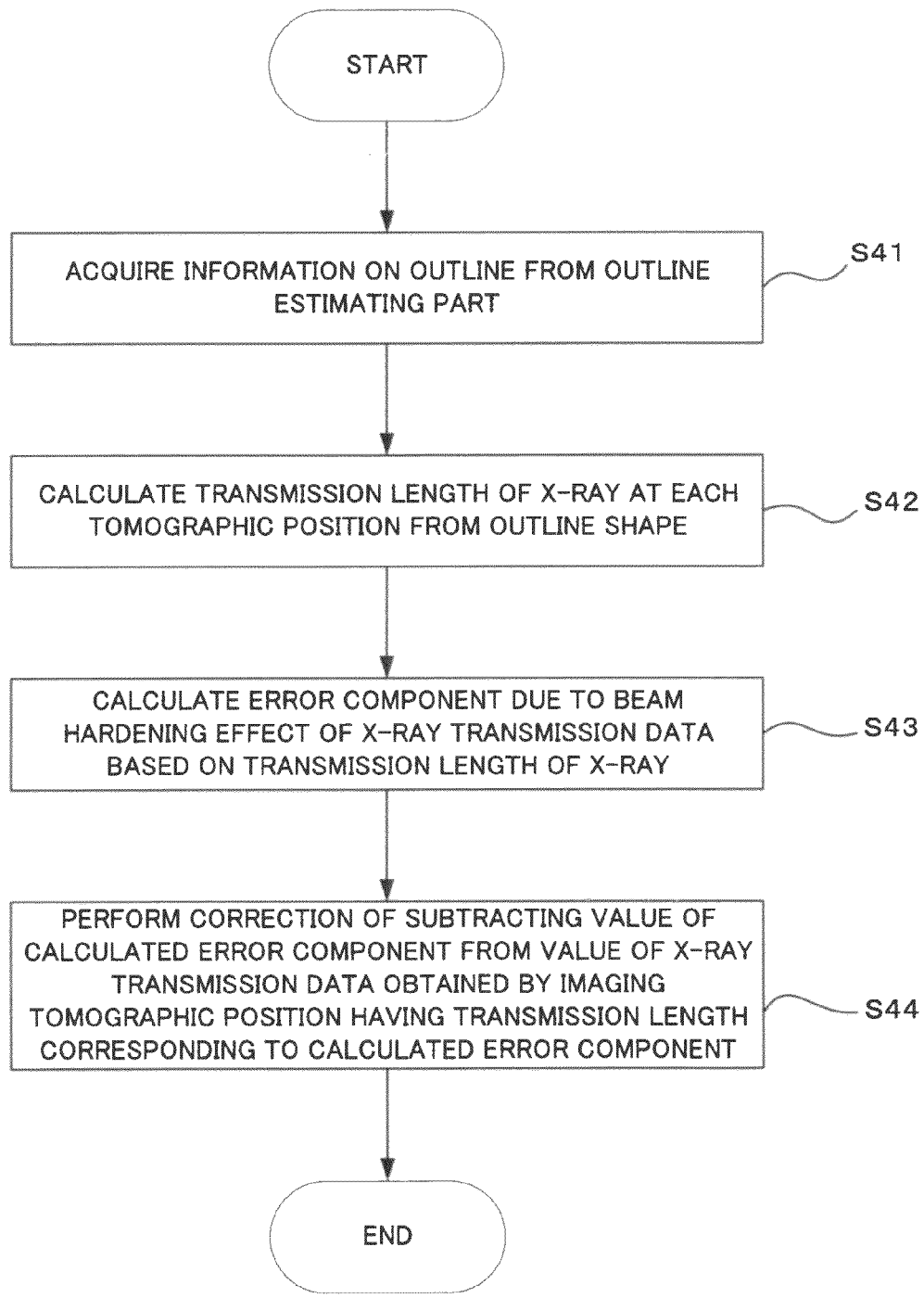
FIG. 16 is a flowchart showing an operation of a BHC process performed by a BHC processor.

FIG. 16 is a flowchart showing an operation of the BHC process performed by the BHC processor 52. Firstly, the BHC processor 52 acquires information on the object outline from the outline estimating part 29 (S41), and calculates the transmission length of the X-ray at each tomographic position from the outline shape shown by the major diameter, the minor diameter and the like (S42).

Figure 17:
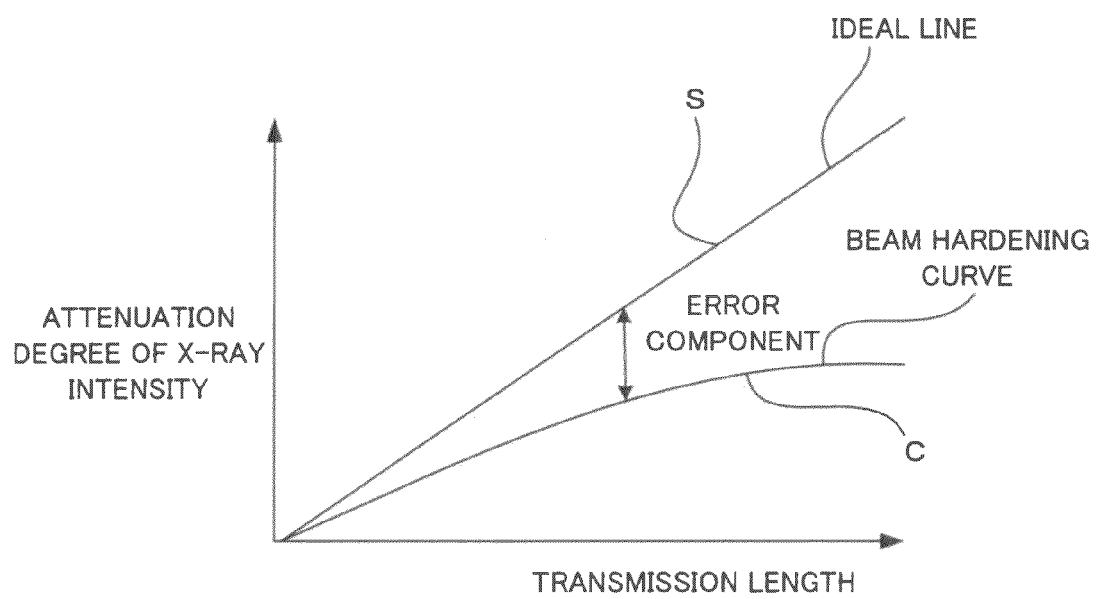
FIG. 17 is a graph showing a relationship between a beam-hardening curve and an ideal line.

Then, based on the calculated transmission length of the X-ray, the BHC processor 52 calculates an error component due to the beam hardening effect of the X-ray transmission data (S43). The BHC processor 52 previously stores a relationship between a beam-hardening curve regarding the attenuation degree of the X-ray intensity corresponding to the transmission length and an ideal curve in the case of no beam-hardening effect as shown in FIG. 17. When calculating the transmission length, the BHC processor 52 calculates the attenuation degree of the X-ray intensity on the ideal curve for the transmission length and the attenuation degree of the X-ray intensity on the beam-hardening curve, and further, calculates a gap between the both, thereby obtaining an error component of the X-ray transmission data obtained by imaging a tomographic position having the transmission length.

When calculating the error component of the X-ray transmission data, the BHC processor 52 performs correction by subtracting the value of the calculated error component from the value of the X-ray transmission data obtained by imaging the tomographic position having the transmission length corresponding to the calculated error component (S44). Consequently, it is possible to obtain the X-ray transmission data from which the influence of the beam hardening effect is removed.

The reconstruction part 53 reconstructs an image of the object P by using the X-ray transmission data corrected by being passed through at least one of the scattered radiation corrector 50, the RASP processor 51, and the BHC processor 52.

The reconstruction part 53 can employ any of various reconstruction methods including the fan-beam convolution back-projection method, the helical interpolation method, the Feldkamp method and the cone beam reconstruction method, by using the X-ray transmission data for approximately 360° of the object P or the X-ray transmission data for 180°+view angle by the half scan method, in order to reconstruct a slice of tomographic image.

The helical interpolation method is a reconstruction method of obtaining by interpolating projection data on the reconstruction surface from the projection data for two rotations or the like that can be used with the fan beam reconstruction method. The Feldkamp method is a reconstruction method in a case where the projection rays crosses with the reconstruction surface like a cone beam. This method is an approximate image reconstructing method of, on condition that a cone angle is small, processing as a fan projection beam at the time of convolution and processing reverse projection along a ray during scan. The cone beam reconstruction method, which is a method that causes less cone angle error than the Feldkamp method, is a reconstruction method of correcting projection data in accordance with a ray angle with respect to the reconstruction surface.

The reconstruction processor 23 corrects the X-ray transmission data by using the outline, and reconstructs an image of the object P from the corrected X-ray transmission data. Then, the display device 27 displays the high-quality image after image processing and correction.

Thus, in the outline estimating method used by the X-ray CT system 10 of the present embodiment, the outline of an object is calculated not from a reconstructed image but from X-ray transmission data obtained by rotating an X-ray tube irradiating X-rays around the object, namely, from X-ray transmission data obtained by full scan. Therefore, there is no need to execute the reconstruction process twice, which increases the real-time characteristic. Moreover, since such a time lag that arises between scanogram imaging and full scan does not arise, decrease of image accuracy due to deviation of the object position does not occur. Accordingly, compared with when obtaining an image reconstructed by using the outline estimated from the scanogram, it is possible to obtain a reconstructed image with significantly high accuracy.

Further, in the reconstruction method used by the X-ray CT system 10 of the present embodiment, the transmission characteristic of the X-ray derived from the object outline is taken into consideration. Therefore, it is possible to effectively execute the scattered radiation correction, the RASP processing or the BHC process, and it is possible to reconstruct an image of as high-quality as that obtained by full scan conforming to an imaging plan based on the object outline obtained from the scanogram.

What is claimed is:

1. An X-ray computed tomography (CT) system, comprising:
  an X-ray tube configured to irradiate an X-ray;
  an X-ray detector situated so as to face the X-ray tube and configured to detect the X-ray having passed through an object;
  a scan controller configured to scan the object by rotating the X-ray tube and the X-ray detector around the object in order to obtain X-ray transmission data by means of the X-ray tube and the X-ray detector, the X-ray transmission data including an entire contour of the object;
  an outline calculator configured to calculate an outline of the object from the X-ray transmission data;
  a correction part configured to correct a distortion of the entire contour of the object indicated by the X-ray transmission data based on the outline calculated by the outline calculator; and a reconstructing part configured to reconstruct image data of an inside of the object based on the X-ray transmission data corrected by the correction part, wherein the outline calculator includes a converter configured to execute fan-parallel conversion on the X-ray transmission data obtained by the scan controller;

an extracting part configured to extract X-ray transmission data of two specific directions orthogonal to each other from the X-ray transmission data to which the fan-parallel conversion is applied; and a calculator configured to calculate the outline of the object by calculating a major diameter, a minor diameter, a shift amount in a major diameter direction, and a shift amount in a minor diameter direction of the object based on the X-ray transmission data of the two specific directions, wherein the calculator is configured to weight and normalize the major diameter, the minor diameter, the shift amount in the major diameter direction, and the shift amount in the minor diameter direction at each tomographic position at which the outline is calculated based on distances between each tomographic position at which the outline is calculated and a tomographic position at which the outline is to be interpolated, in order to interpolate the outline.

2. The X-ray CT system according to claim 1, wherein the calculator is configured to calculate the outline of the object at a tomographic position represented by the X-ray transmission data of each specific direction, based on the X-ray transmission data of each specific direction; and the calculator includes an interpolating part configured to interpolate, based on the outline of the object at the tomographic position represented by the X-ray transmission data of each specific direction, the outline at a position other than the tomographic position.

3. The X-ray CT system according to claim 1, wherein the extracting part is configured to extract the X-ray transmission data of three or more specific directions from the X-ray transmission data to which the fan-parallel conversion is applied; and the calculator is configured to calculate the major diameter, the minor diameter, the shift amount in a major diameter direction, the shift amount in a minor diameter direction, and an inclination of the object based on the X-ray transmission data of the three or more specific directions.

4. The X-ray CT system according to claim 1, wherein: the reconstructing part includes a scattered-radiation corrector configured to eliminate scattered-radiation components from the X-ray transmission data based on the outline.

5. The X-ray CT system according to claim 1, wherein: the reconstructing part includes a beam hardening correction (BHC) part configured to correct an effect of a beam-hardening effect from the X-ray transmission data based on the outline.

6. The X-ray CT system according to claim 1, wherein: the reconstructing part is configured to selectively pass the X-ray transmission data through a low-pass filter based on the outline and to reconstruct the image data of the inside of the object from the X-ray transmission data filtered out by the low-pass filter.

7. An object-outline estimating method, comprising: obtaining X-ray transmission data of an object, the X-ray transmission data including an entire contour of the object;

executing fan-parallel conversion on the obtained X-ray transmission data;

extracting X-ray transmission data of two specific directions orthogonal to each other from the X-ray transmission data to which the fan-parallel conversion is applied;

calculating an outline of the object by calculating a major diameter, a minor diameter, a shift amount in a major diameter direction, and a shift amount in a minor diameter direction of the object based on the X-ray transmission data of the two specific directions; and correcting a distortion of the entire contour of the object indicated by the X-ray transmission data based on the calculated outline, wherein the calculating step includes weighting and normalizing the major diameter, the minor diameter, the shift amount in the major diameter direction, and the shift amount in the minor diameter direction at each tomographic position at which the outline is calculated based on distances between each tomographic position at which the outline is calculated and a tomographic position at which the outline is to be interpolated, in order to interpolate the outline.

8. The object-outline estimating method according to claim 7, wherein:

the calculating step comprises calculating the outline of the object at a tomographic position represented by the extracted X-ray transmission data, wherein the method further comprises interpolating, based on the outline of the object at the tomographic position represented by the X-ray transmission data of each specific direction, the outline at a position other than the tomographic position.

9. The object-outline estimating method according to claim 7, wherein:

X-ray transmission data of three or more directions is extracted from the X-ray transmission data to which the fan-parallel conversion is applied; and the calculating step comprises calculating an inclination of the object based on the X-ray transmission data of the three or more directions.

10. An image reconstructing method of reconstructing X-ray transmission data obtained by rotating an X-ray tube irradiating an X-ray around an object into an image of an inside of the object, the image reconstructing method comprising:

executing fan-parallel conversion on the obtained X-ray transmission data, the X-ray transmission data including an entire contour of the object;

extracting X-ray transmission data of two specific directions orthogonal to each other from the X-ray transmission data to which the fan-parallel conversion is applied;

calculating an outline of the object by calculating a major diameter, a minor diameter, a shift amount in a minor diameter direction, and a shift amount in a minor diameter direction of the object based on the extracted X-ray transmission data of the two specific directions;

correcting a distortion of the entire contour of the object indicated by the X-ray transmission data based on the calculated outline; and reconstructing the image of the inside of the object based on the X-ray transmission data corrected in the correcting step, wherein the calculating step includes weighting and normalizing the major diameter, the minor diameter, the shift amount in the major diameter direction, and the shift amount in the minor diameter direction at each tomographic position at which the outline is calculated based on distances between each tomographic position at which the outline is calculated and a tomographic position at which the outline is to be interpolated, in order to interpolate the outline.

11. The image reconstructing method according to claim 10, wherein:
in the correcting step, scattered-radiation components are eliminated from the X-ray transmission data based on the outline; and
the image of the inside of the object is reconstructed from the X-ray transmission data from which the scattered-radiation components have been eliminated.

12. The image reconstructing method according to claim 10, wherein:
in the correcting step, an effect of a beam-hardening effect is corrected from the X-ray transmission data based on the outline; and
the image of the inside of the object is reconstructed from the X-ray transmission data in which the effect of the beam-hardening effect has been corrected.

13. The image reconstructing method according to claim 10, wherein:
in the correcting step, the X-ray transmission data is selectively passed through a low-pass filter based on the outline; and
the image of the inside of the object is reconstructed from the X-ray transmission data from which the noise has been eliminated by the low-pass filter.

* * * * *